(12) United States Patent
Koseki

(10) Patent No.: US 6,854,598 B2
(45) Date of Patent: Feb. 15, 2005

(54) CONTAINER FOR HOLDING CURVED NEEDLES

(75) Inventor: Tomoaki Koseki, Toshima-ku (JP)

(73) Assignee: Koseki Medical K.K., Tokyo (JP)

( * ) Notice: Subject to any disclaimer, the term of this patent is extended or adjusted under 35 U.S.C. 154(b) by 162 days.

(21) Appl. No.: 10/139,015

(22) Filed: May 2, 2002

(65) Prior Publication Data

US 2003/0188982 A1 Oct. 9, 2003

(30) Foreign Application Priority Data

Apr. 8, 2002 (JP) ........................................ 2002-104645

(51) Int. Cl.[7] .............................................. A61B 17/06
(52) U.S. Cl. ....................... 206/380; 206/63.3; 206/560
(58) Field of Search ................ 206/63.5, 363, 206/477, 478, 480, 483, 380, 564, 565, 560, 63.3

(56) References Cited

U.S. PATENT DOCUMENTS

| | | | |
|---|---|---|---|
| 1,644,830 A | | 10/1927 | Henderson |
| 3,768,635 A | * | 10/1973 | Eggert .......................... 206/366 |
| 4,182,448 A | | 1/1980 | Huck et al. |
| 4,243,140 A | | 1/1981 | Thrun |
| 4,260,056 A | | 4/1981 | Hovarth et al. |
| 4,344,532 A | | 8/1982 | Eldridge, Jr. et al. |
| 4,415,089 A | | 11/1983 | Ruffa |
| 4,591,048 A | | 5/1986 | Eldridge, Jr. |
| 4,596,329 A | | 6/1986 | Eldridge, Jr. |
| 5,131,533 A | * | 7/1992 | Alpern ....................... 206/63.3 |
| 5,180,053 A | * | 1/1993 | Cascio et al. ............... 206/63.3 |
| 5,350,060 A | * | 9/1994 | Alpern et al. ............... 206/63.3 |
| 5,469,689 A | | 11/1995 | Demarest et al. |
| 5,733,293 A | * | 3/1998 | Scirica et al. ................ 606/144 |

FOREIGN PATENT DOCUMENTS

| | | |
|---|---|---|
| JP | 60-25218 Y2 | 7/1985 |
| JP | 61-16165 B2 | 4/1986 |
| JP | 2-42025 U | 3/1990 |
| JP | 8-243110 A | 9/1996 |
| JP | 9-75405 A | 3/1997 |
| JP | 2001-224603 A | 8/2001 |

* cited by examiner

Primary Examiner—David T. Fidei

(57) ABSTRACT

A container for holding curved needles has side fixation hooks in pairs and a center fixation hook projected from a bottom plate to fix a needle by putting the needle between the hooks and in which the tip of the needle falls down securely to a fixed direction. In case of holding plural needles, plural side fixation hooks and center fixation hooks are molded to project continuously in a line from the bottom plate and so the backs of the hooks are united with one another.

2 Claims, 1 Drawing Sheet

CONTAINER FOR HOLDING CURVED NEEDLES

BACKGROUND OF THE INVENTION

1. Field of the Invention

The present invention relates to a container for holding curved needles such as surgical suture needles or fishhooks.

2. Description of the Related Art

A container that holds curved needles and in which tips of the needles fall down securely to a fixed direction has not been developed.

SUMMARY OF THE INVENTION

The sharp tip of a curved needle turns upwardly depending on the way of holding it so it is very dangerous to hold a used surgical suture needle because there is a possibility of infection. The volume of a container increases when holding a standing needle.

A container of the present invention has the following structure to achieve the above-mentioned problems. Side fixation hooks for fixing both sides of the center part of a needle project in pairs from the surface of a bottom plate. A center fixation hook for fixing the center of needle also projects between and a little away from the side fixation hooks from the surface of the bottom plate and the upper part of the center fixation hook extends to be located between the side fixation hooks. Springy material is used for the center fixation hook. The upper parts of the center fixation hook and the side fixation hooks bend to face each other. When a needle is inserted from the upper part of the center fixation hook, the needle is pushed to the channel of the side fixation hooks by the springy force and that enables the tip of the needle to fall down securely to a fixed direction.

In case of holding plural needles, plural side fixation hooks and center fixation hooks are molded to project continuously in a line from the bottom plate and so the backs of the hooks are united with one another.

DESCRIPTION OF THE PREFERRED EMBODIMENTS

Figure 1:
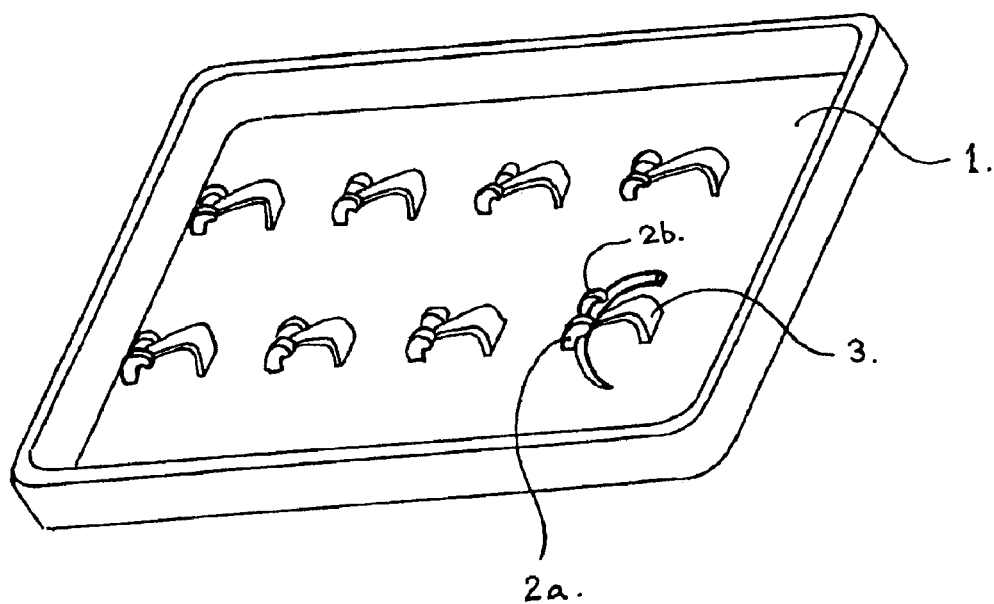
FIG. 1 is an outside view of a container for holding curved needles.

The present invention is described below referring to the drawing. FIG. 1 shows an embodiment according to claim 1. Side fixation hooks 2a, 2b and a center fixation hook 3, which face to each other, project continuously from the surface of a bottom plate 1. When a needle is inserted from the upper part of the center fixation hook 3, the needle is pushed to the channel of the side fixation hooks 2a and 2b by the springy force and that enables the tip of the needle to fall down securely to a fixed direction. Indicating numbers on sides of the hooks enables it to be used as a needle counter for used suture needles. Making a lid of the container transparent makes easier to confirm the kind and the number of needles. The bottom plate and the lid are molded with resin such as ABS. Polystyrene, Polypropylene, or Polyethylene, and it is possible to produce them in large quantities. Increasing the number of hooks and molding the backs of each hook to be united with one another enable to hold many needles according to claim 2.

Figure 2:
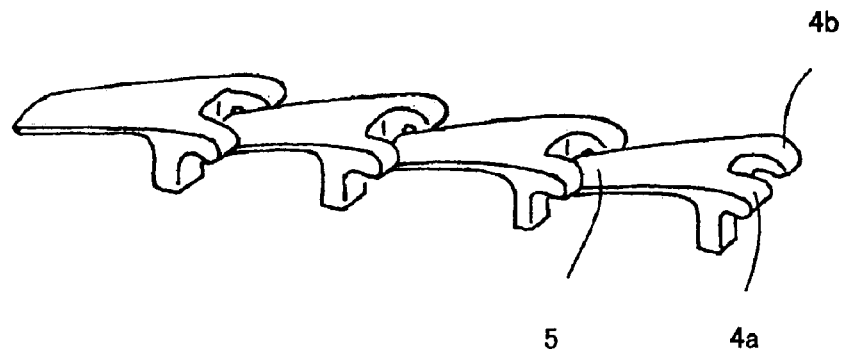
FIG. 2 is an outside view of a serial of hooks made as one part, wherein the hooks are for holding curved needles.

FIG. 2 shows the hook part of hook storage cases wherein the back side of each hook is made by solid body mould method. The upper part of center fixation hook 5 extends to the location between a pair of side fixation hooks 4a and 4b, sandwiched between the tow hooks, and the back side of the hooks are united as one solid body. This form enables this cart to be more compact, and enables more needles to be stored.

Work efficiency will be improved because the tip of a needle falls down securely to a fixed direction when the needle is inserted. It will be safe with no anxiety about infection because the sharp tip of the needle is pressed down to the surface of a bottom plate. The size of a container as a whole will be compact because the container can hold the needles flatly.

What is claimed is:

1. A container for holding curved needles such as surgical suture needles or fishhooks wherein the base of the container is in a plate form surrounded by edges, characterized in that side fixation hooks for fixing both sides of the center part of the needle in its longitudinal direction, the needle project in pairs from the surface of a bottom plate, a center fixation hook for fixing the center of needle in its longitudinal direction also projects between and a little away from the side fixation hooks from the surface of the bottom plate, (the upper part in its longitudinal direction of the center fixation hook extends to be located between the side fixation hooks, springy material is used for the center fixation hook, the upper parts in the longitudinal direction of the center fixation hook and the side fixation hooks bend to face each other, the inner part formed by the bending is referred to as a channel, and the tip point of the needle in the longitudinal direction falls down securely to a fixed direction because the needle is pushed to the channel of the side fixation hooks by the springy force when a needle is inserted from the upper part of the center fixation hook, and the upper part of the center fixation hook bends as much as the thickness of the needle.

2. A container for holding curved surgical suture needles or fishhooks as claimed in claim 1, characterized in that plural side fixation hooks and center fixation hooks are molded to project continuously in a line from the bottom plate and so the backs of the hooks are united with one another in order to hold plural needles, as shown in FIG. 2.

* * * * *